(12) United States Patent
Tsai

(10) Patent No.: US 8,275,188 B2
(45) Date of Patent: Sep. 25, 2012

(54) SYSTEM AND METHOD FOR INSPECTING CHIPS IN A TRAY

(75) Inventor: Cheng Tao Tsai, Hsinchu County (TW)

(73) Assignee: Cheng Mei Instrument Technology Co., Ltd., Hsinchu County (TW)

( * ) Notice: Subject to any disclaimer, the term of this patent is extended or adjusted under 35 U.S.C. 154(b) by 803 days.

(21) Appl. No.: 12/342,586

(22) Filed: Dec. 23, 2008

(65) Prior Publication Data

US 2009/0169094 A1 Jul. 2, 2009

(30) Foreign Application Priority Data

Dec. 31, 2007 (TW) .............................. 96151366 A

(51) Int. Cl.
*G06K 9/00* (2006.01)

(52) U.S. Cl. ......... 382/149; 382/144; 382/145; 382/147

(58) Field of Classification Search .................. 382/144, 382/145, 141, 147, 149
See application file for complete search history.

(56) References Cited

U.S. PATENT DOCUMENTS

| | | | | |
|---|---|---|---|---|
| 6,301,398 B1 * | 10/2001 | Kimball et al. | ............... | 382/319 |
| 6,541,747 B1 * | 4/2003 | Kikuchi et al. | ............... | 382/149 |
| 7,692,144 B2 * | 4/2010 | Watanabe et al. | ............. | 356/631 |
| 2007/0148792 A1 * | 6/2007 | Marx et al. | ....................... | 438/14 |

FOREIGN PATENT DOCUMENTS

| | | |
|---|---|---|
| JP | 8248443 | 9/1996 |
| JP | 2000266691 | 9/2000 |

OTHER PUBLICATIONS

Office Action dated Jun. 2, 2010 for 200810004725.2, which is a corresponding Chinese application that cites JP8248443A and JP2000266691A.

* cited by examiner

*Primary Examiner* — Gregory J Toatley
*Assistant Examiner* — Iyabo Alli
(74) *Attorney, Agent, or Firm* — WPAT, P.C.; Anthony King

(57) ABSTRACT

A system for inspecting chips in a tray comprises a three-dimensional sensor, a focus computing unit, an image sensor and a focusing device. The three-dimensional sensor is used to obtain the height signals of surfaces of the chips. The focus computing unit calculates the focusing positions of chips. The surface inspection sensor is used to inspect the surfaces of the chips. The focusing device is used to bring the images of the surfaces of the chips into the focus of the image sensor.

26 Claims, 13 Drawing Sheets

SYSTEM AND METHOD FOR INSPECTING CHIPS IN A TRAY

BACKGROUND OF THE INVENTION

1. Field of the Invention

The present invention relates to a system for inspecting chips, and more particularly, to a system for inspecting chips in a tray.

2. Description of the Related Art

Due to the compact and high performance requirement of electronics, the technologies of both integrated circuit (IC) design and manufacturing, as well as IC packaging, are advancing steadily. In the case of liquid crystal display (LCD) technology, for example, when a WXGA LCD is introduced by replacing a VGA LCD, the display panel circuitry becomes more complex due to the higher resolution. If the number of LCD driver ICs is not increased, every LCD driver IC must have more pins or ports. Under such circumstances, COF (Chip On Film) or COG (Chip On Glass) bonding techniques are gradually becoming more popular than TAB (Tape Automated Bonding) technique for this type of technology development. In directly attached to the electrode pads of the LCD panel, which can reduce tape cost. The cost of TAB tape is high, more than 70% of the total packaging cost. Therefore, the cost advantage of COG bonding technique is very appealing. Although COG bonding technique has cost advantage, the manufacturer still cannot substitute COG bonding technique for TAB technique. This is due to the fact that in the COG technique the driver ICs are directly mounted onto panel glass, making rework very difficult in cases where a driver IC has a driving problem. The problematic driver IC must be removed from the panel glass, and this process is very troublesome. Improved inspection of driver ICs prior to bonding is a key step to improve the efficiency, and thus the popularity, of the COG technique.

In wafer packaging technology the gold bumps on a chip are inspected at the wafer level; many testing-equipment producers offer products to automate steps of this inspection process. After gold bump inspection, the chips may be damaged or contaminated between the dicing process and the final test, and there is currently no process for inspection of every chip among these steps. At present, statistical process control procedures are used to monitor the quality of chips. Because not every chip is inspected after gold bump inspection, the production yield is difficult to control, which affects the willingness of producers to adopt the COG technique.

The first problem to be overcome while inspecting diced chips in a tray is how to perform the chip focusing. A tray is usually a plastic injection molded product. As plastic molded products often suffer warping or deformation, they often have imprecise dimensions. As a result, the chips in a tray will fluctuate in height or lie at an angle, creating problems for an automated chip inspection system. A common solution to the height fluctuation is coarse and fine focus adjusting mechanisms. That is to say, the height of a chip will be brought into focus by the coarse focus mechanism, which has wider depth of focus and lower magnification capabilities, and then the height of the chip will be further adjusted by the fine focus mechanism, which has higher magnification capabilities and narrower depth of focus. Finally, the chip can be inspected under high magnification. This solution suffers from slow throughput and cannot meet the requirements of the packaging industry, as it is not suitable for continuous high-speed inspection situations.

The present invention proposes a solution, which can directly inspect chips in tray at high throughput rates, for the above problems and the urgent requirement of the chip packaging industry.

SUMMARY OF THE INVENTION

The present invention proposes a system for inspecting chips in a tray, which comprises a three-dimensional sensor configured to provide a height signal of a surface of a chip in a tray, a focus computing unit configured to determine a focusing position of the surface of the chip based on the height signal, an image sensor configured to inspect the surface of the chip and a focusing device configured to provide the image sensor to perform focusing operation by the focusing position, wherein the image sensor is attached to the focusing device.

The present invention proposes a method for inspecting chips in a tray, which comprises scanning a plurality of chips in a tray and obtaining a height signal of each chip by a three-dimensional sensor, processing the height signal of each chip to determine focusing position thereof, adjusting the focus of an image sensor by the focusing position of each chip; and inspecting a surface of each chip by the image sensor.

BRIEF DESCRIPTION OF THE DRAWINGS

The invention will be described according to the appended drawings in which.

PREFERRED EMBODIMENT OF THE PRESENT INVENTION

Figure 1:
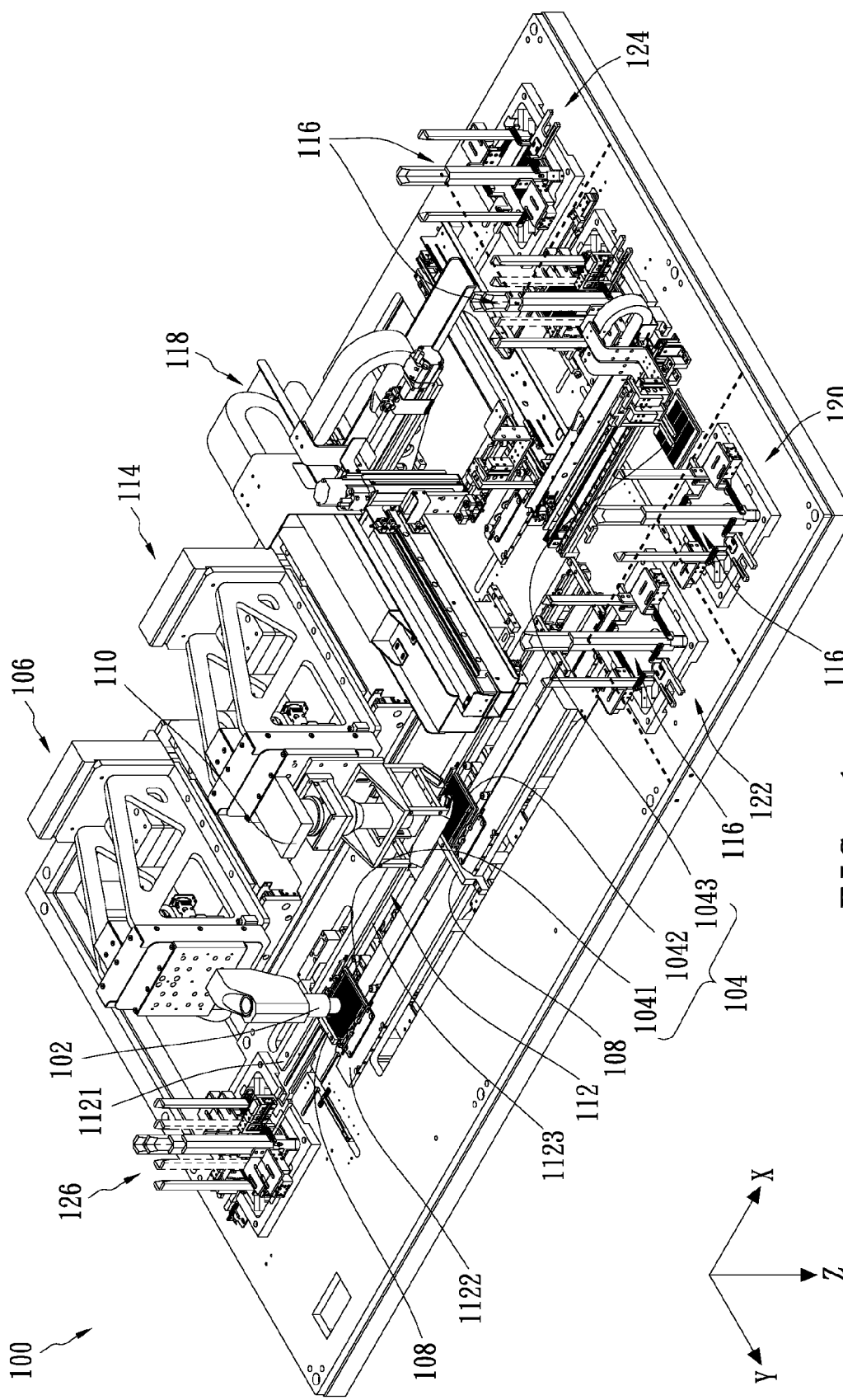
FIG. 1 shows a system for inspecting chips in a tray according to one embodiment of the present invention.

FIG. 1 shows a system 100 for inspecting chips in a tray according to one embodiment of the present invention. The system 100 of the present invention is primarily for the inspection of defects on surfaces of chips in a tray. The tray used to hold chips is a plastic molded product. Due to plastic warp deformation, chips held in the tray will fluctuate in height, and the height fluctuation is a challenge to high-resolution inspection. Hence, the first consideration for the inspection of defects on surface is how to bring the surface to be inspected into focus. The next consideration is the method of performing focusing. Different approaches will result in different throughput and have different effects on the packaging process. In addition, if an inspection lot has a large number of chips and each chip goes through focusing and inspection procedures, it will be difficult to have a high throughput when an unsuitable inspection method is chosen. Giving consideration to both high-resolution and high throughput capabilities is an objective of the present invention, with a particular goal being a system that can inspect defects on chips held by any kind of chip carriers without any side effect and still have high inspection throughput with a large quantity of chips. The method proposed by the present invention first measures the focusing position of each inspection target, and then inspects defects by the focusing position. When the system 100 provided by the present invention starts to inspect defects on surfaces of chips in a tray, a three-dimensional sensor 102 will measure the height of the surface of each chip held in a tray 1041, which carries a plurality of chips. The weights of some kinds of chips are minimal, for example the COG chips, and therefore the measurement is performed by moving the three-dimensional sensor 102 for the avoidance of the effects of chip movement or vibration on accuracy. The three-dimensional sensor 102 is attached to a first movement stage 106, and because the first movement stage 106 can move in three directions, the three-dimensional sensor 102 can scan in a horizontal plane and move in the direction orthogonal to the plane. The three-dimensional sensor 102 is primarily used to get the height signals of the surface to be inspected from each chip in the tray 1041. The three-dimensional sensor 102 performs chip scan one after another and gather the height signals of the surfaces of all chips in the tray 1041, and thereafter the height signals are processed to determine the coordinates of the focusing positions of the chips.

After the focusing position processing step is finished, the tray 1041 is moved to the place underneath an imaging device 110, where the tray 1042 of FIG. 1 is located, by a push bar mechanism 108 of a transfer mechanism 400. A tray 104 moves in a tray track 112 during the entire inspection process. Two parallel, elongated metal plates 1121 and 1122 form the tray track 112. The two metal plates 1121 and 1122 are separated by a distance slightly larger than the width of the tray 104, and therefore the tray 104 can move in between the two metal places 1121 and 1122. To minimize inspection errors, potential errors from all kind of sources have to be evaluated when the system 100 is designed and manufactured. The error sources have to be removed if possible, or else the effects of the errors have to be compensated for the accuracy of inspection. Because the locations of the three-dimensional sensor 102 and the imaging device 110 are different in this embodiment, the height difference between the two locations and the sloping surfaces of the two locations all contribute to potential measurement errors. Thus, the surface 1123 flatness of the entire tray track 112 is very important. In one embodiment of the system 100 of the present invention, the surface planar deviation is less than 5 micrometers. The imaging device 110 is configured to inspect defects on the surface of chips in the tray 1042, and is driven by a second movement stage 114 for inspecting and focus adjusting. In the inspection procedure for each chip, the imaging device 110 is first moved to the location of a chip in the tray 1042, and then the height of the imaging device 110 is adjusted by the focusing position, which is processed based on the measurement of the three-dimensional sensor 102, for focusing. After the focusing is finished, the imaging device 110 starts to inspect defects on the surface of the chip.

After all chips in tray 104 are finished with defect inspection and if all chips are qualified, the tray 104 will be moved to the front of a first unloading zone 120, where the tray 1043 is as illustrated in FIG. 1, and then the tray 104 will be unloaded to a tray handling apparatus for unloading 116. If some chips are defective, the defective chips will be picked up from the tray 104 by a chip pickup apparatus 118. The selected chips are collected and sent to the tray handling apparatus for unloading 116 at a disqualified zone 124. After the defective chips are picked up, the tray 104 is then moved to the tray handling apparatus for unloading 116 at a second unloading zone 122. When an operator starts to perform the chip inspection process, he/she puts a tray stack into a tray handling apparatus for loading 126. The tray handling apparatus for loading 126 then loads trays 104 in sequence from the bottom of the tray stack into the system 100 for inspection.

Figure 2A:
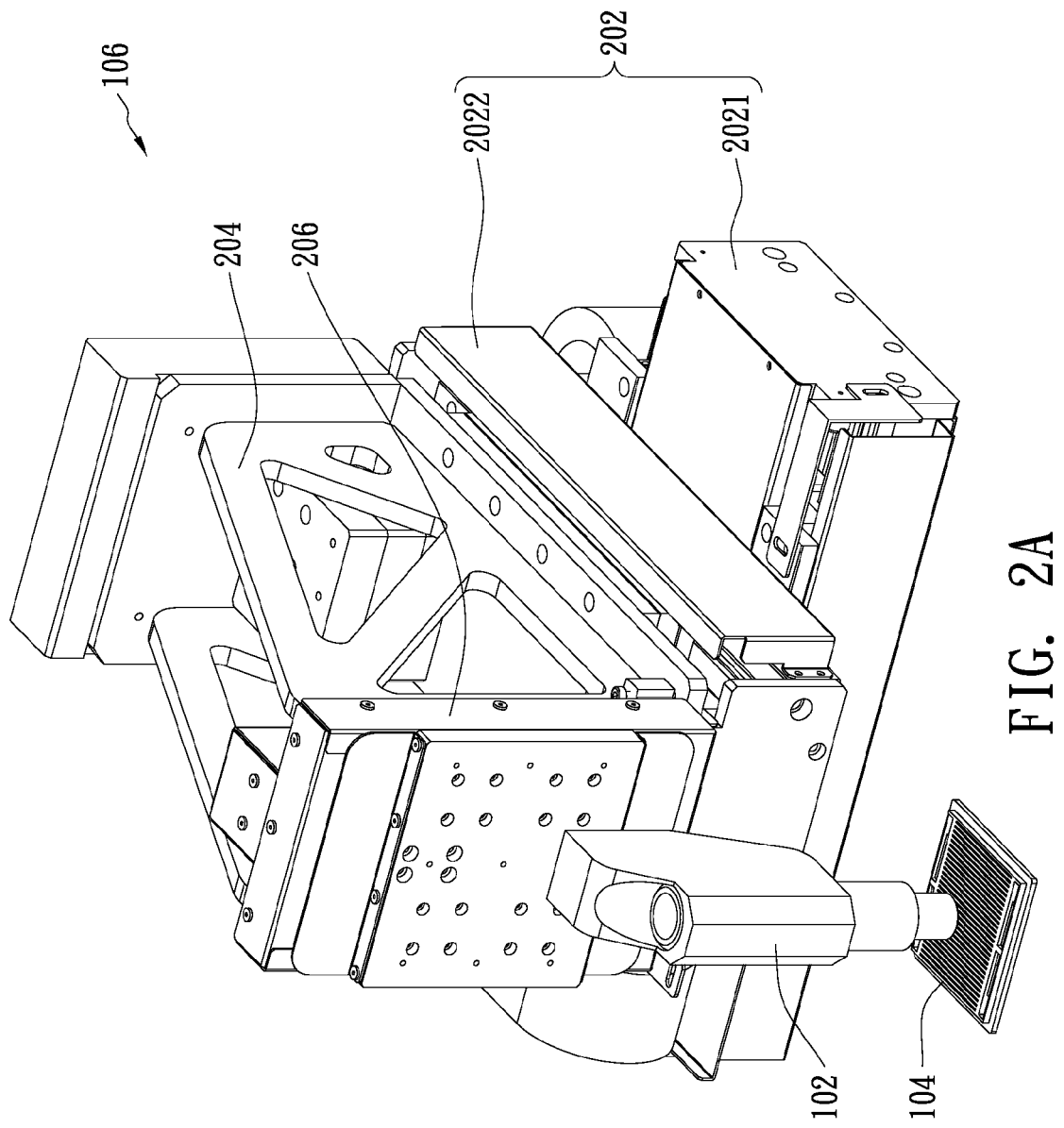
FIG. 2A shows a three-dimensional sensor 102 and a first movement stage 106 according to one embodiment of the present invention.

FIG. 2A shows a three-dimensional sensor 102 and a first movement stage 106 according to one embodiment of the present invention. A first movement stage 106 comprises an XY stage 202 and a Z stage 206. The XY stage 202 comprises a single-axial direction movement stage 2021 moving in the X-axis direction and another one axial direction movement stage 2022 moving in the Y-axis direction. A frame 204 is set upon the XY stage 202, and the Z stage 206 is vertically attached to the frame 204. A three-dimensional sensor 102 attached to the Z stage 206 can move in three directions by the first movement stage 106.

Figure 2B:
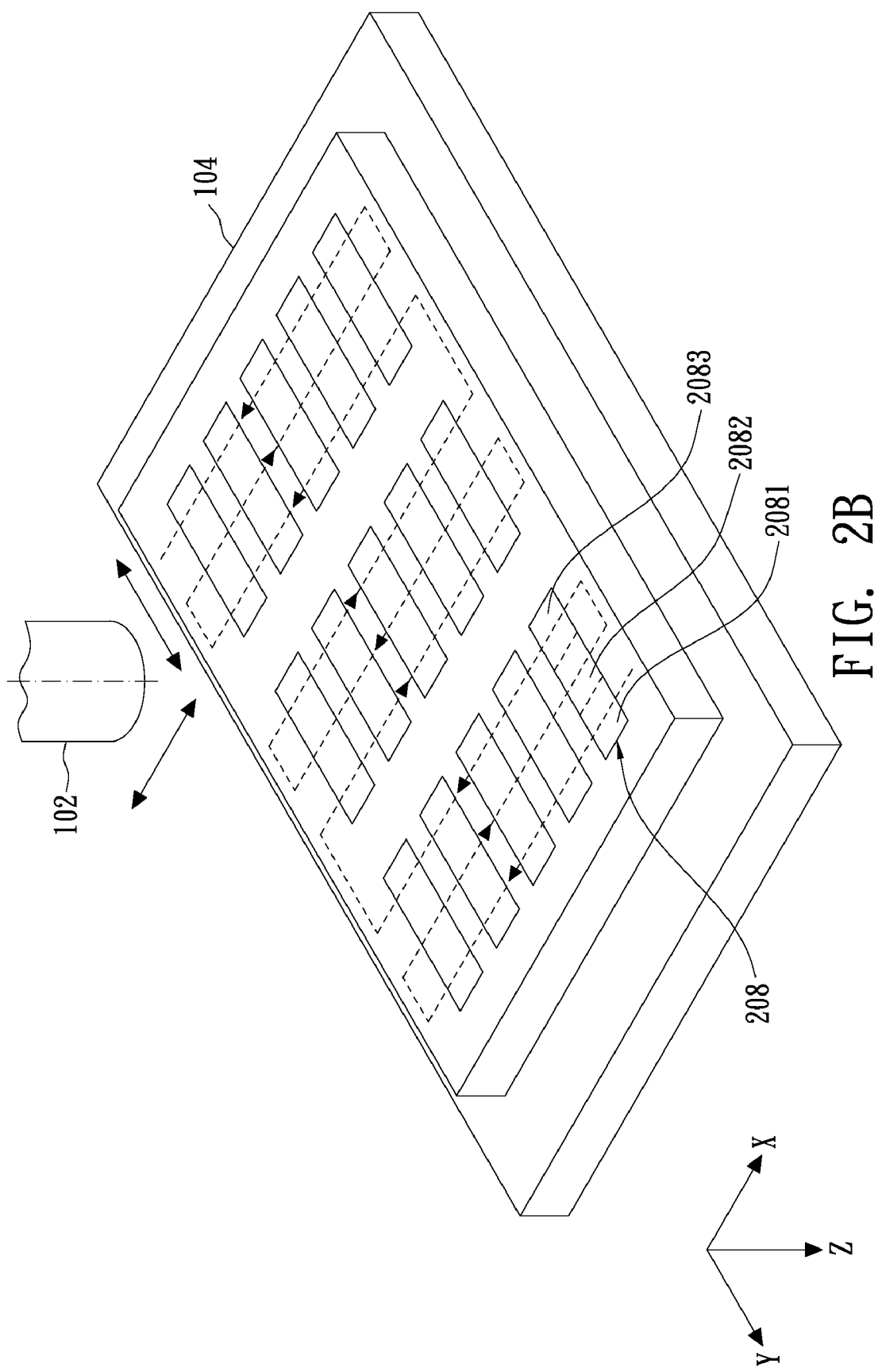
FIG. 2B illustrates a scanning route of a three-dimensional sensor 102 according to one embodiment of the present invention.

FIG. 2B illustrates a scanning route of a three-dimensional sensor 102 according to one embodiment of the present invention. In principle, the three-dimensional sensor 102 measures the heights of surfaces of chips in a tray 104 by moving back and forth in the X-axis direction to scan the center of each chip. The surface height of each chip is an average of a plurality of sampling signals. If a chip has an elongated shape, the differences between the center and the two ends of the chip may be beyond the depth of focus of the imaging device 110. In such circumstance, the elongated chip 208 can be divided into three inspected areas 2081, 2082, and 2083 as illustrated in FIG. 2B, and the three-dimensional sensor 102 can scan the center part of each area 2081, 2082, or 2083 for measuring the height of each area to be inspected.

The measurement of a surface height of a chip is by optical technique, due to the high speed of the optical technique. The three-dimensional sensor 102 can be a chromatic sensor. The chromatic sensor receives light having different wavelengths reflected from a chip surface. With a different height of the chip, different wavelength light passes through a pinhole located at the focus point of the reflected light. By measuring the wavelength of the passed light, the height of the chip can be determined.

Figure 2C:
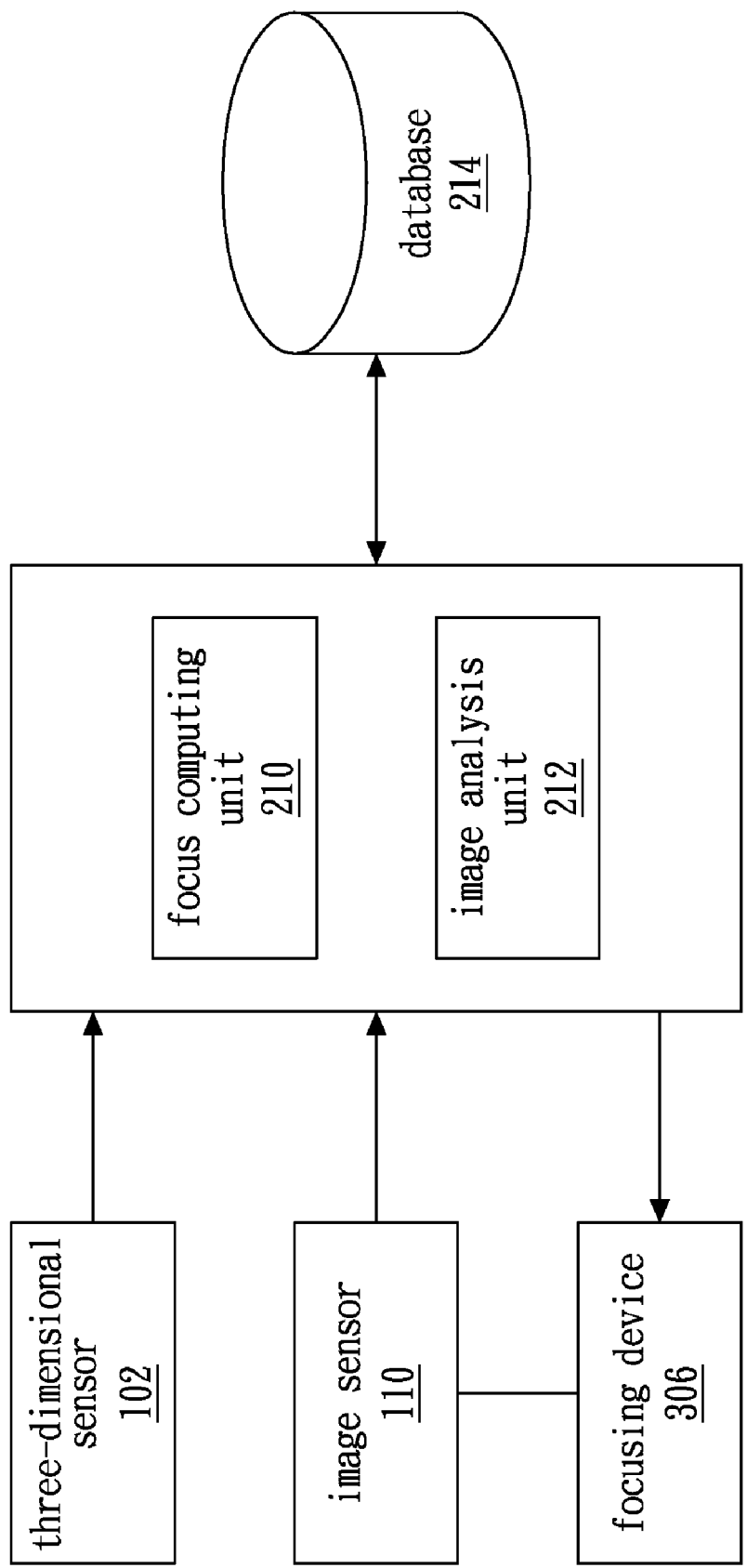
FIG. 2C shows a block diagram of the measuring and inspecting operations according to one embodiment of the present invention.

FIG. 2C shows a block diagram of the measuring and inspecting operations according to one embodiment of the present invention. While measuring chip heights, the system 100 performs sampling on the signals generated by the three-dimensional sensor 102 and stores the sample data in a database 214. A focus computing unit 210 performs averaging operations on the sample data and transforms the averaged result into focusing position coordinates, which are stored in the database 214 and used for defect inspection.

Figure 3A:
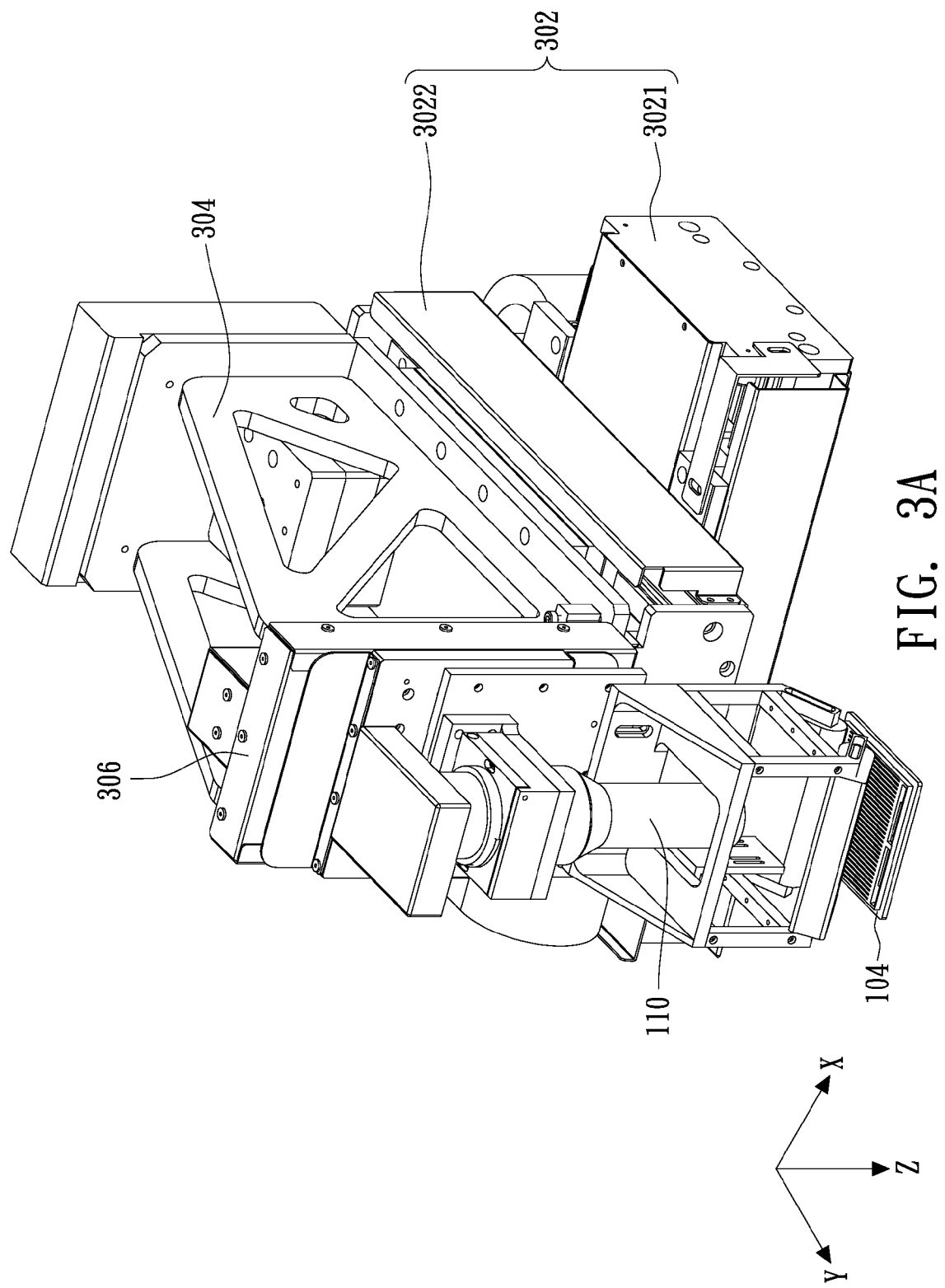
FIG. 3A shows an image sensor 110 and a second movement stage 114 according to one embodiment of the present invention.

FIG. 3A shows an image sensor 110 and a second movement stage 114 according to one embodiment of the present invention. A second movement stage 114 comprises an XY stage 302 and a focusing device 306. The XY stage 302 comprises a single-axial direction movement stage 3021 moving in the X-axis direction and another one axial direction movement stage 3022 moving in the Y-axis direction. A frame 304 is set upon the XY stage 302, and the focusing device 306 is vertically attached to the frame 304. An imaging device 110 attached to the focusing device 306 can move in three dimensions by the second movement stage 114 for inspecting defects of chips. In one embodiment, the focusing device 306 can be a Z stage.

Figure 3B:
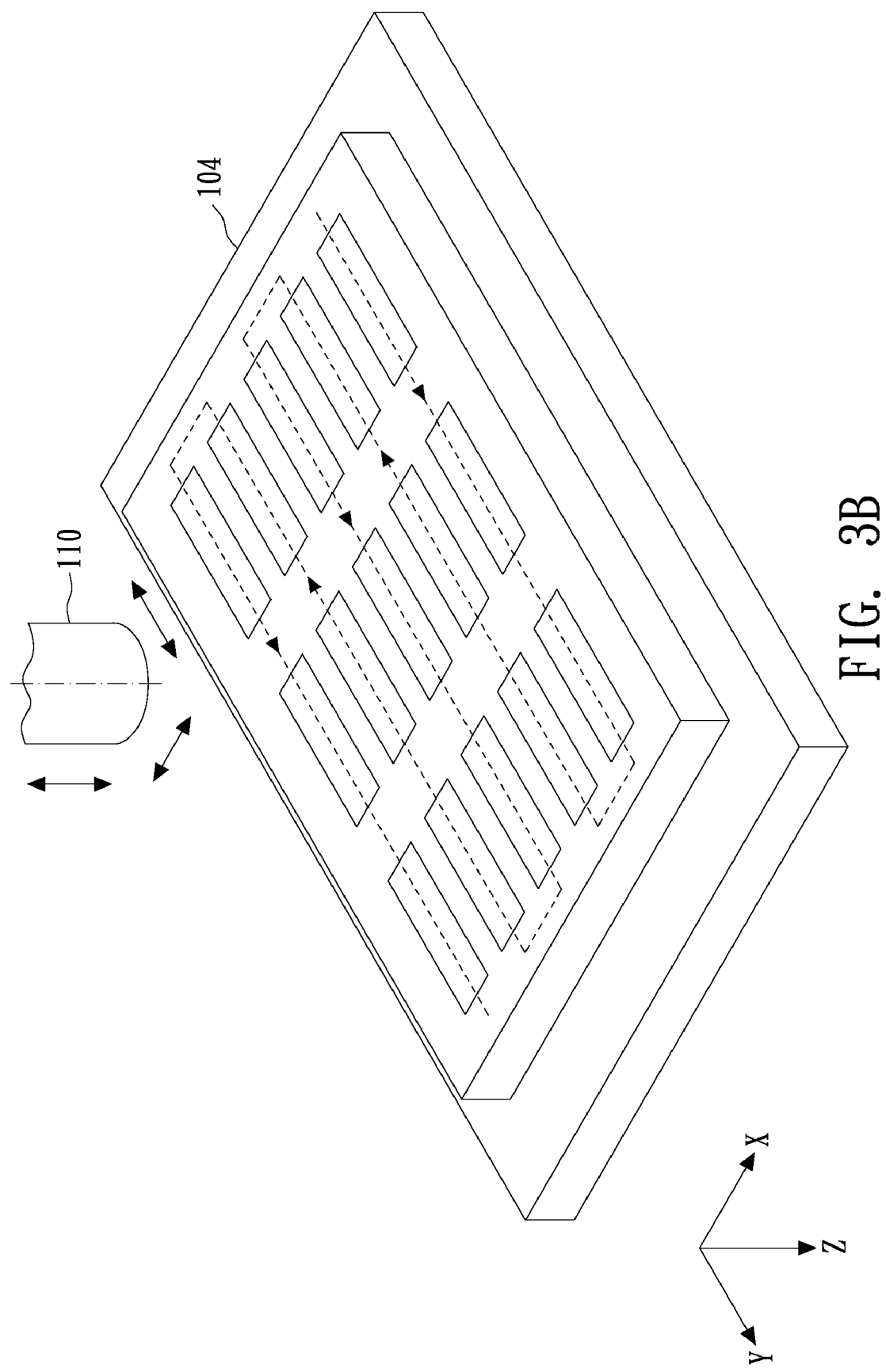
FIG. 3B illustrates a scanning route of an imaging device 110 according to one embodiment of the present invention.

FIG. 3B illustrates a scanning route of an imaging device 110 according to one embodiment of the present invention. Referring to FIGS. 2C and 3B, the imaging device 110 inspects surfaces of chips in a tray 104 sequentially in the Y direction (which may be along the chip's long side). For each inspection, the focusing position of the chip is initially retrieved, and then the focusing device 306 is moved to a position that puts the surface to be inspected within the depth of focus of the imaging device 110, and finally the inspection is performed. If the chip is divided into several inspected areas, the imaging device 100 will be focused on each inspected area by its corresponding focusing position first, and then will perform each inspection. An image analysis unit 212 analyzes the images obtained by the imaging device 110 and stored in a database 214, and the analysis results are compared to predetermined specifications. If the analysis result doesn't meet the specifications, the image analysis unit 212 will record the corresponding chip location in the tray 104. In one embodiment, the image sensor 110 can be a charge coupled device or a complementary metal oxide semiconductor sensor.

Figure 4:
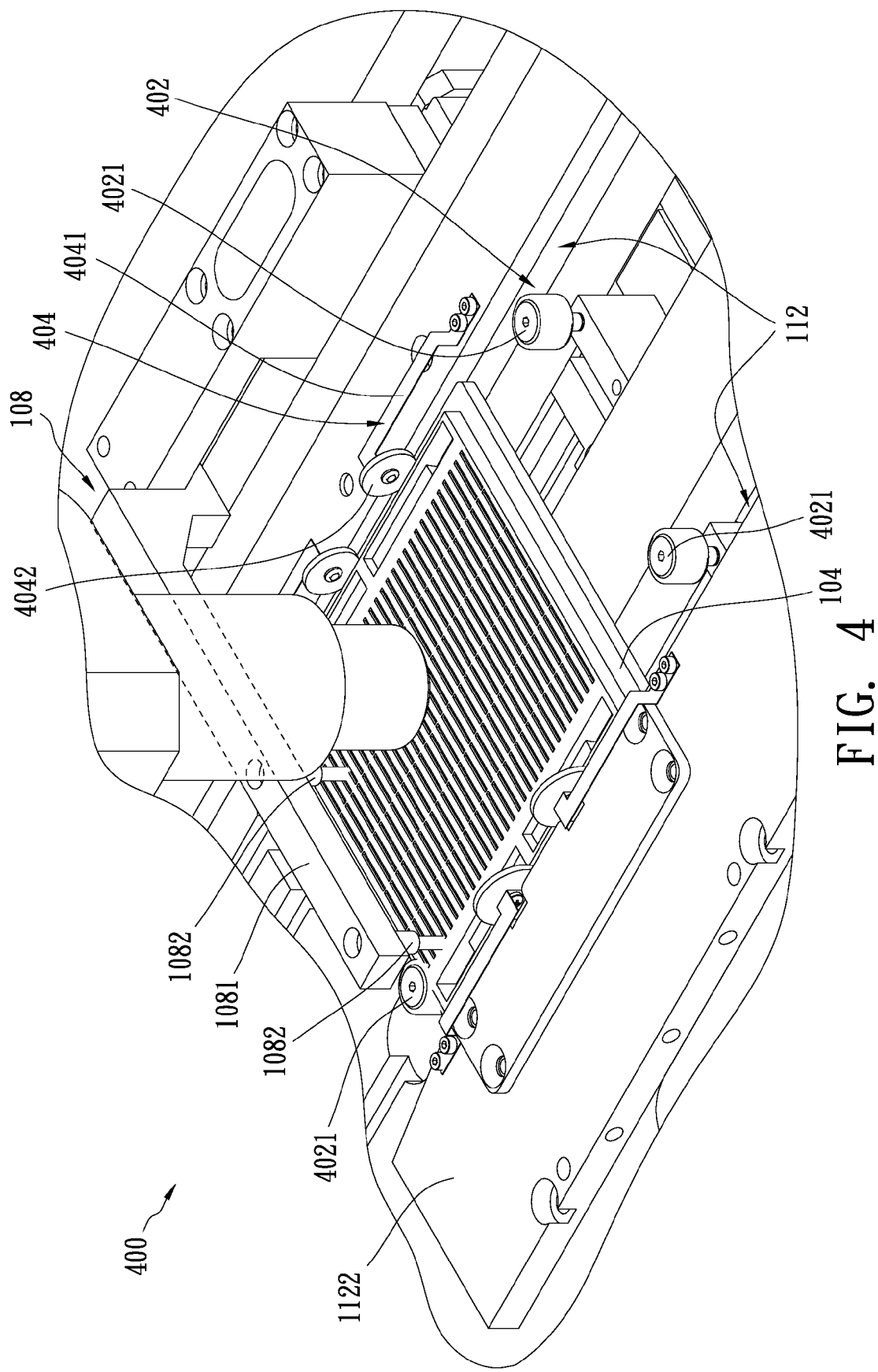
FIG. 4 shows a transfer mechanism 400 according to one embodiment of the present invention.

FIG. 4 shows a transfer mechanism 400 according to one embodiment of the present invention. During the inspection process, the tray 104 in the tray track 112 is moved using a push bar mechanism 108. The push bar mechanism 108 comprises a push bar 1081, which stretches over the tray track 112, and the portion of the push bar 1081 above the tray track 112 includes a contact part 1082. When the push bar 1081 moves, the contact part 1082 pushes the tray 104 to move along the tray track 112. In this embodiment, the contact part 1082 includes a plurality of vertical pins. The push bar 1081 is attached to a linear driving apparatus (not shown), and the linear driving apparatus (not shown) may be a combination of a motor and a rack/pinion mechanism.

The tray 104 is held steadily during inspection by a pinch roller mechanism 404. Each pinch roller mechanism 404 uses an elastic member 4041 to provide the pinch roller 4042 attached thereto with a pressing force, and the tray 104 pressed under the pressing force through the pinch roller 4042 can be inspected without any influence of vibration. In this embodiment, the elastic member 4041 of the pinch roller mechanism 404 can be a spring arm.

A positioning apparatus 402 is used to position and orientate a tray 104. The positioning apparatus 402 comprises an up/down movement mechanism. There are a plurality of extruded parts 4021, which have wheel-like shape and are on two opposite sides of the tray 104, on the top of the positioning apparatus 402. The positioning apparatus 402 positions and orientates the tray 104 by placing it between the extruded parts 4021. The extruded parts 4021 moving through a surface slot are usually hidden below the surface of the tray track 112, and therefore will not interfere with the tray 104 movement. The vertical displacement of the positioning apparatus 402 is driven by an up/down movement mechanism (not shown), and the up/down movement mechanism may be a linear motor, a hydraulic cylinder or an electrical actuator. When the extruded parts 4021 of a positioning apparatus 402 are protruded into the tray track 112, the position and orientation of the tray 104 located above the positioning apparatus 402 are adjusted by lateral forces exerted by the lateral surfaces of the extruded parts 4021.

Figure 5:
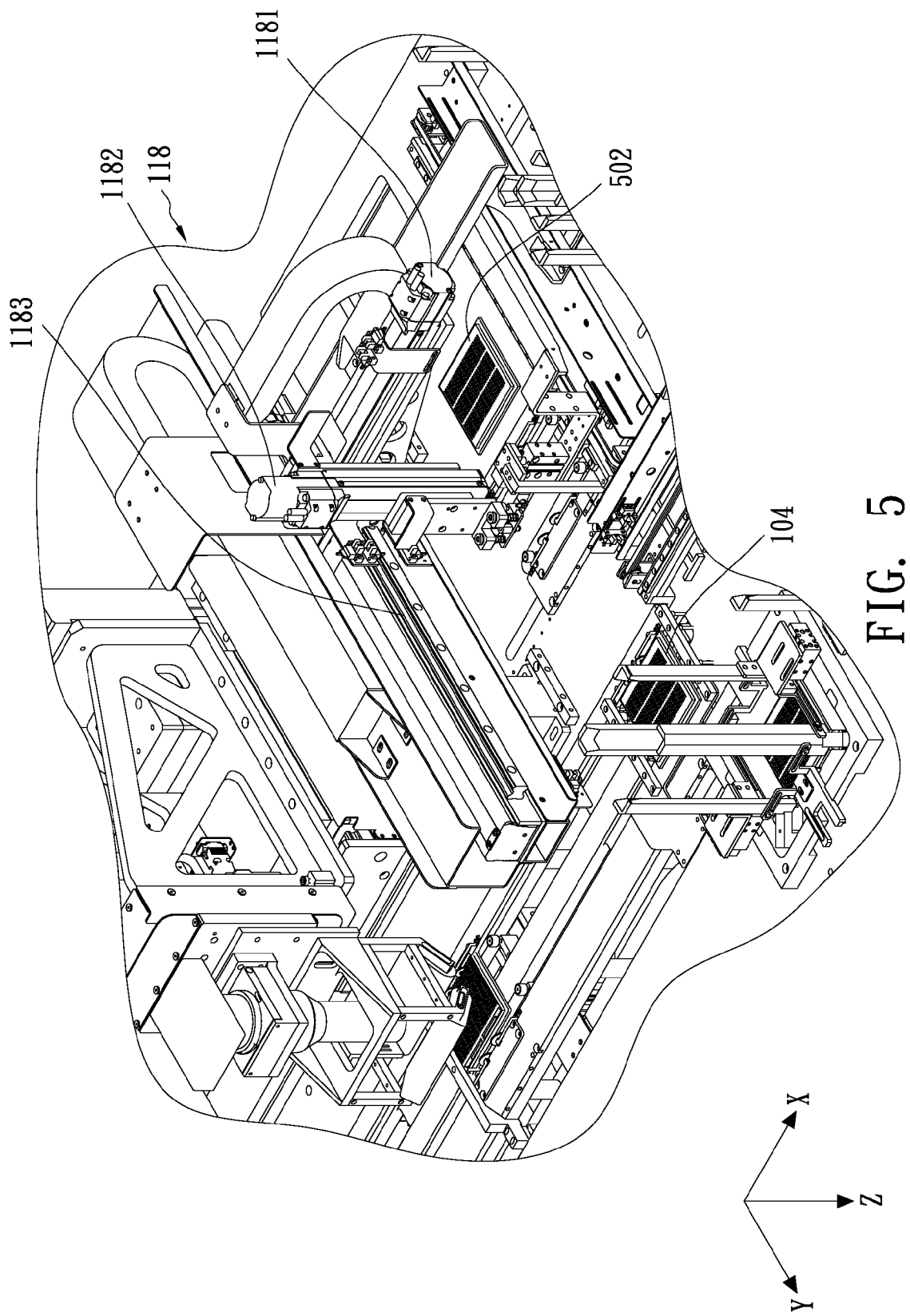
FIG. 5 shows a chip pickup apparatus 118 according to one embodiment of the present invention.

FIG. 5 shows a chip pickup apparatus 118 according to one embodiment of the present invention. If there is a defective chip in a tray 104, the defective chip will be picked up and placed in a recovery tray 502 by a chip pickup apparatus 118. The pickup apparatus 118 includes an X-axis direction linear motor 1183, a Y-axis direction linear motor 1181 and a Z-axis direction linear motor 1182 for moving horizontally and vertically. The pickup apparatus 118 can include any kind of end effector (not shown) for handling chips, for example a vacuum nozzle end effector.

Figure 6:
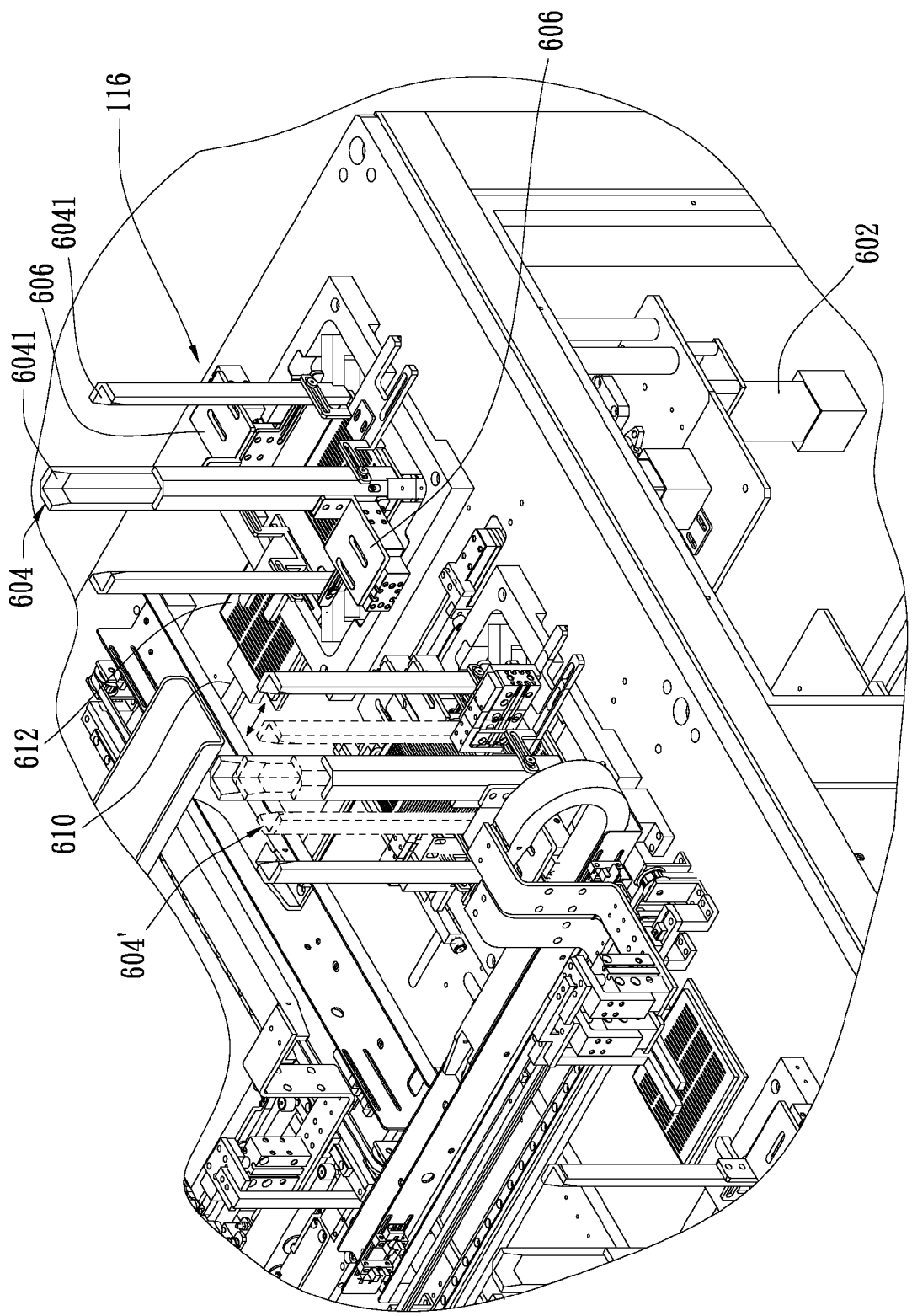
FIG. 6 shows a tray handling apparatus for unloading 116 according to one embodiment of the present invention.

FIG. 6 shows a tray handling apparatus for unloading 116 according to one embodiment of the present invention. A tray handling apparatus for unloading 116 comprises a support frame adjustment apparatus 602, an elevator apparatus (not shown) and a support frame 604. The support frame 604 comprises a plurality of frame members 6041, the cross-section shape of which is an L, used for supporting and guiding while a tray stack moves up or down. If the size of inspected trays 104 is smaller, the frame members 6041 of the support frame 604 can be adjusted to fit the size, illustrated as the support frame 604', through the support frame adjustment apparatus 602. The elevator apparatus comprises a driving device and the driving device can be a servomotor. A tray 612 is moved in the tray handling apparatus for unloading 116 by a loading arm 610. The method of unloading initially moves the tray 612 into the interior of the tray handling apparatus for unloading 116. The elevator apparatus (not shown) moves the tray 612 up until the tray 612 touches the tray stack(s) held by a holding device 606. Next, the elevator apparatus (not shown) moves the tray 612 and the tray stack up one tray height distance after the holding device 606 releases the tray stack. Thereafter, the holding device 606 holds the tray 612. Finally, the elevator apparatus (not shown) is replaced to its initial position. The tray 612 can be moved to the front of the tray handling apparatus for unloading 116 by a push bar mechanism (not shown) and then moved by the tray handling apparatus for unloading 116 by the loading arm 610, and by these steps, an inspected tray 612 can be unloaded. In one embodiment, the elevator apparatus (not shown) comprises a lead screw/servomotor combination for up/down driving.

Figure 7:
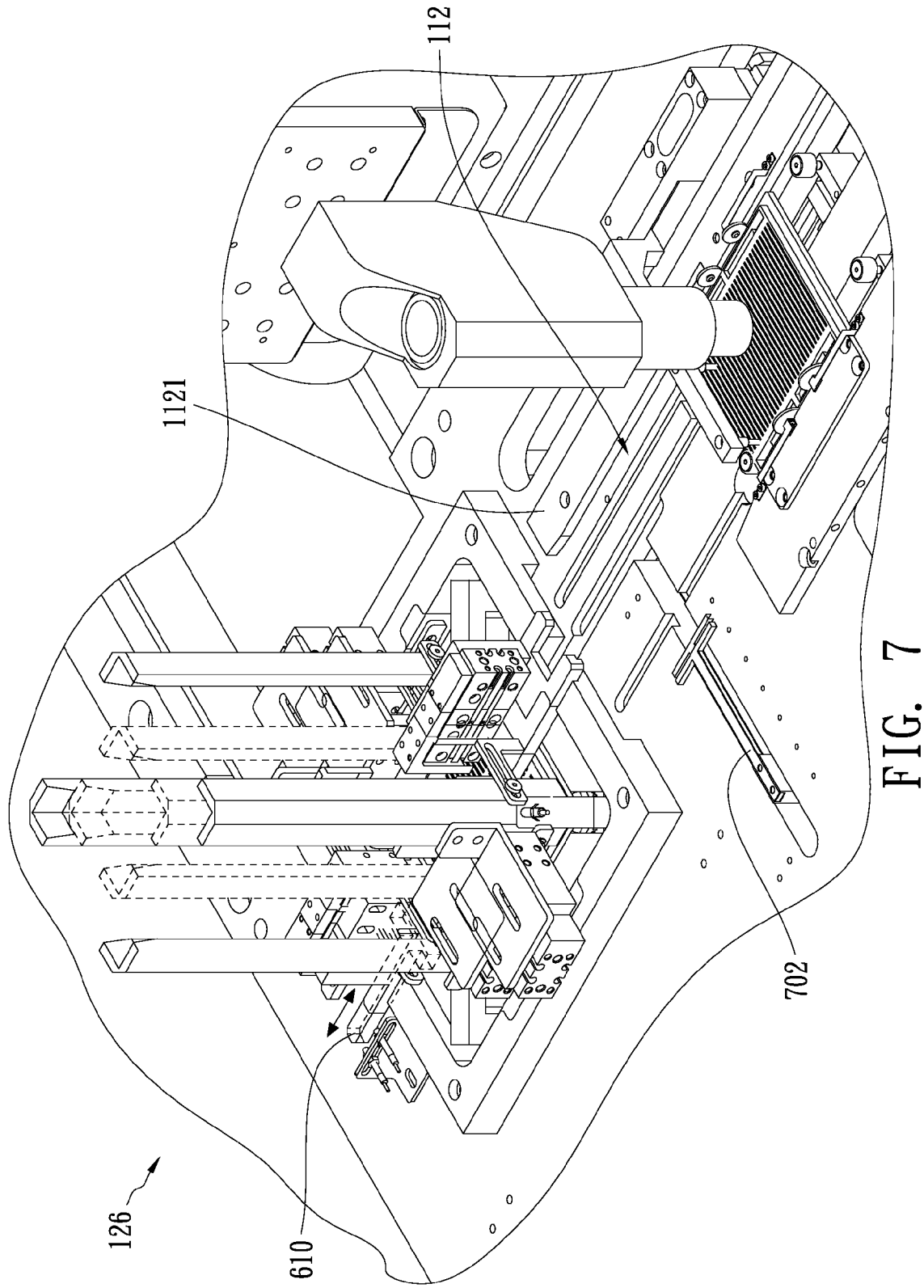
FIG. 7 shows a tray handling apparatus for loading 126 according to one embodiment of the present invention.

FIG. 7 shows a tray handling apparatus for loading 126 according to one embodiment of the present invention. The tray handling apparatus for loading 126 has structures similar to the tray handling apparatus for unloading 116, but trays 104 are moved out of the tray handling apparatus for loading 126 by a loading arm 610. The trays 104 in the tray handling apparatus for loading 126 are moved out in a bottom-up sequence. When a tray 104 is going to be inspected, the elevator apparatus (not shown) will bring its bottom level with the top surface of the system 100 first after it is released. Then, the loading arm 610 pushes it out of the tray handling apparatus for loading 126. Finally, the tray 104 will be pushed against the elongated metal plate 1121 of the tray track 112 by an alignment arm 702 for aligning the tray track 112, and the tray 104 can travel along the tray track 112.

Figure 8:
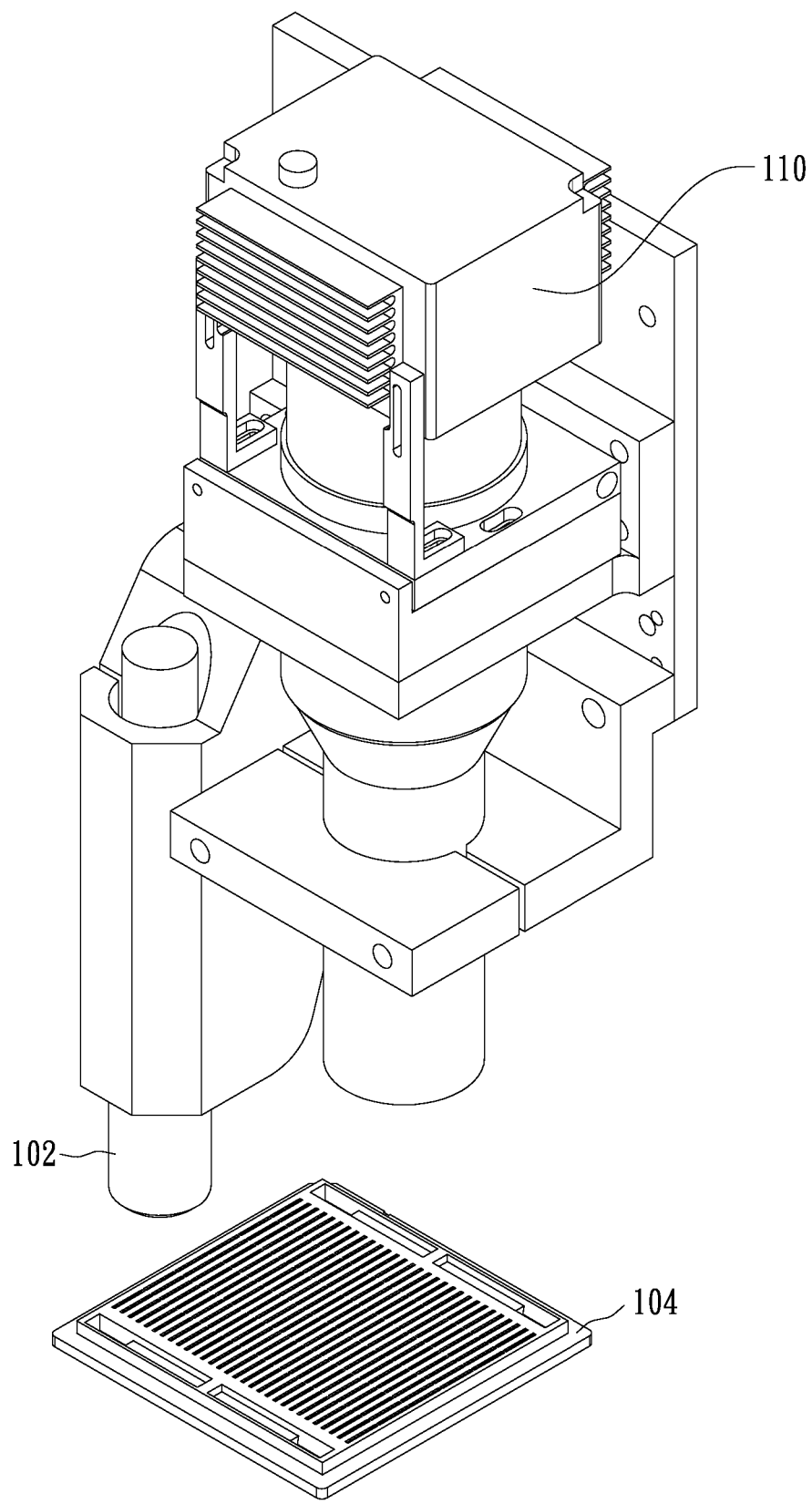
FIG. 8 shows integration of the three-dimensional sensor 102 and the image sensor 110 according to one embodiment of the present invention.

FIG. 8 shows integration of the three-dimensional sensor 102 and the image sensor 110 according to one embodiment of the present invention. The three-dimensional-sensor 102 and the image sensor 110 can be driven by a first movement stage 106 and a second movement stage 114 separately as illustrated in FIG. 1. The three-dimensional-sensor 102 and the image sensor 110 can also be disposed on the same movement stage. For example, the three-dimensional sensor 102 can be disposed on the focusing device 306 together with the image sensor 110. A tray 104 can be measured and inspected by the sensors both at the same location in the arrangement. One advantage of this arrangement is there is no error caused by different locations, and another advantage is the saving of space.

Figure 9:
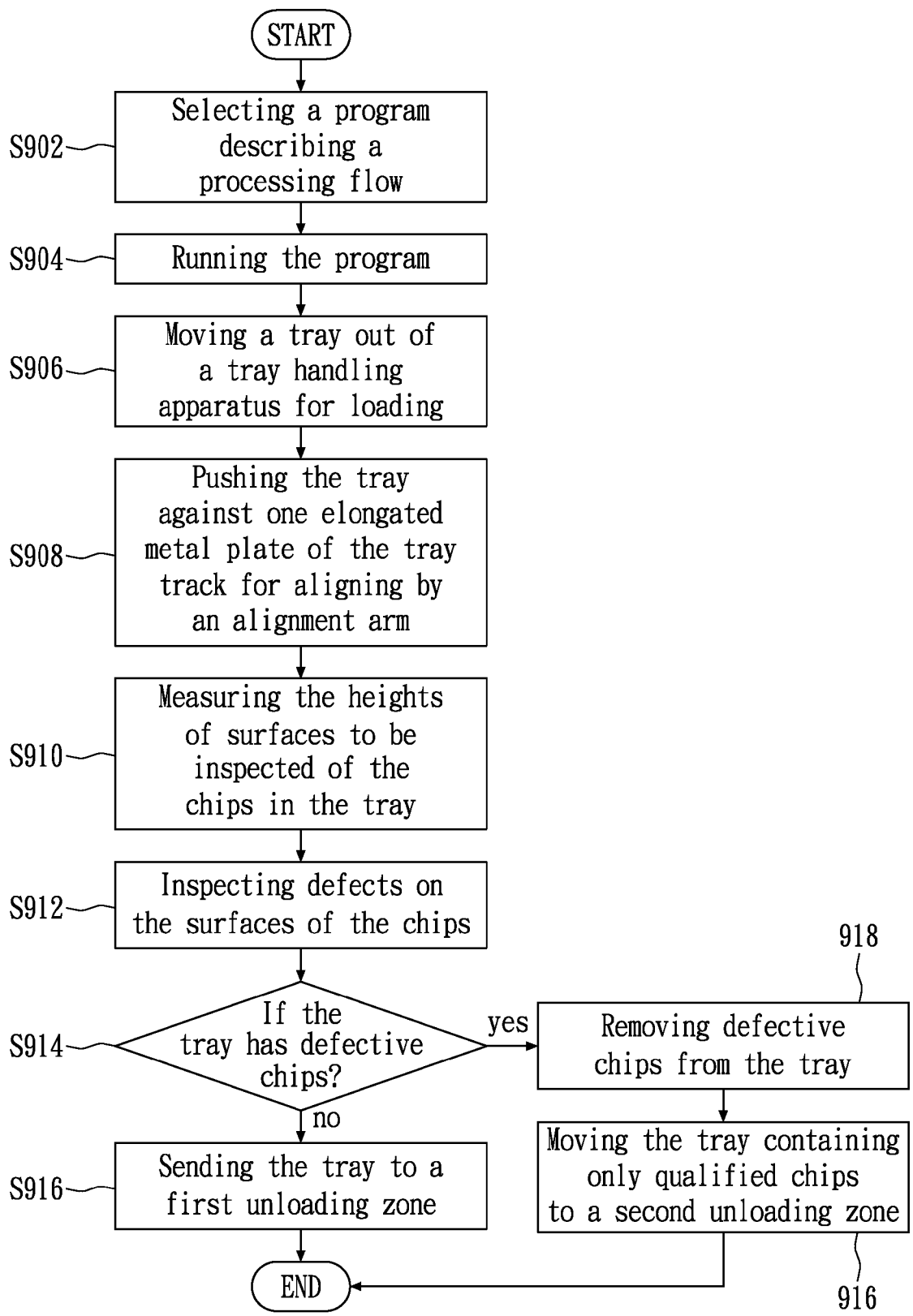
FIG. 9 is the flow chart of a system for inspecting chips in a tray according to one embodiment of the present invention.

FIG. 9 is the flow chart of a system for inspecting chips in a tray according to one embodiment of the present invention. In step S902, an operator selects a program describing a processing flow. In step S904, the operator runs the program. In step S906, a tray is moved out of a tray handling apparatus for loading and is prepared for inspection operation. In step S908, an alignment arm pushes the tray against one elongated metal plate of the tray track for aligning. In step S910, the tray is moved to below a three-dimensional sensor, and the three-dimensional sensor measures the heights of surface to be inspected of the chips in the tray; the measured height signals are processed into focusing positions of the chips. In step S812, based on the focusing positions, an image sensor performs focusing and inspecting defects on the surfaces of the chips. The images obtained by the image sensor are analyzed, and the locations of defective chips disqualified by the analysis results are recorded. In step S914, the system determines if the tray has defective chips. In step S916, if the tray has no defective chips, the tray is sent to a first unloading zone. In step S918, the defective chips are removed from the tray. In step S920, the tray containing only qualified chips is moved to a second unloading zone.

Figure 10:
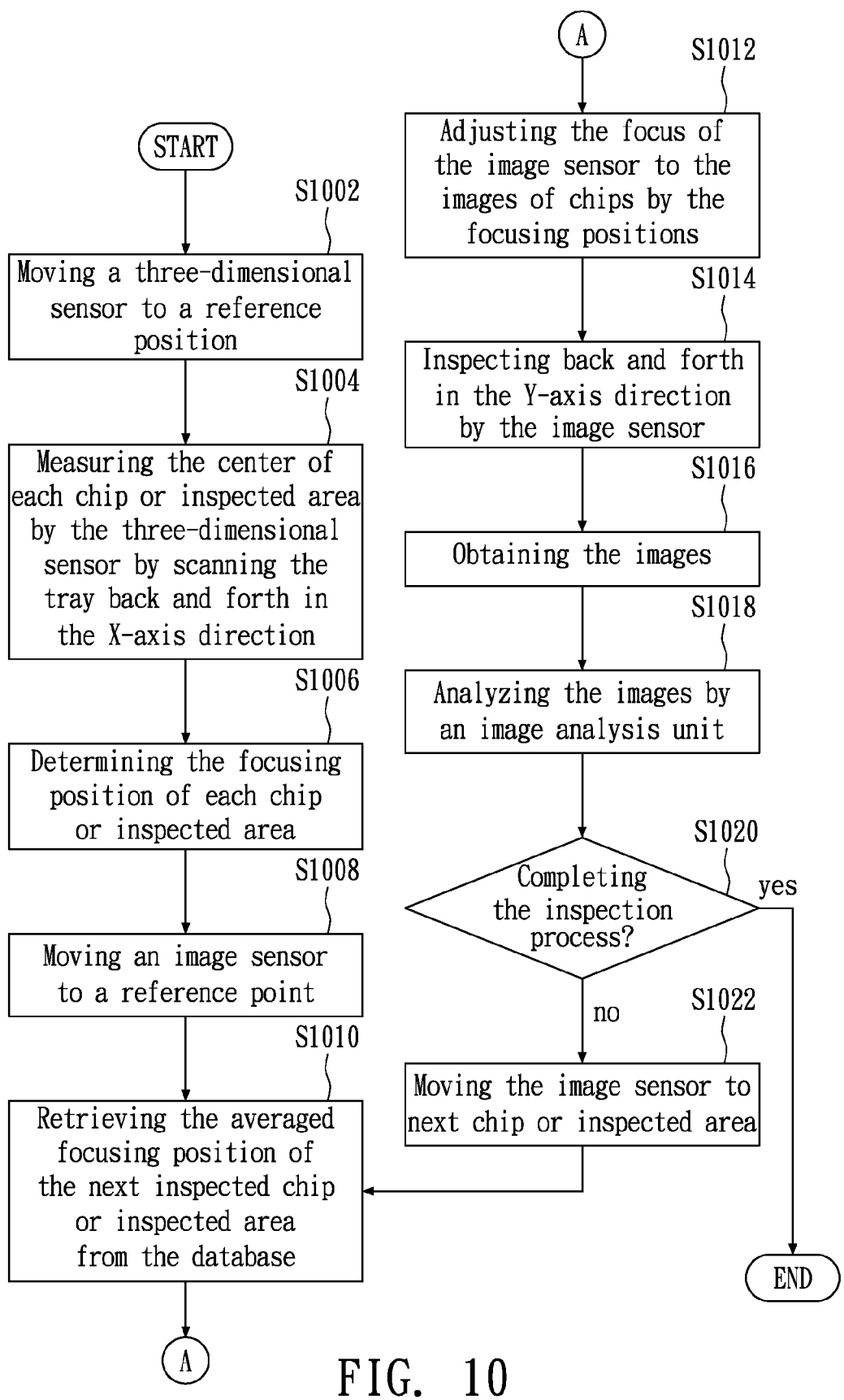
FIG. 10 is the flow chart of the steps performed in an inspection operation according to one embodiment of the present invention.

FIG. 10 is the flow chart of the steps performed in an inspection operation according to one embodiment of the present invention. In step S1002, a three-dimensional sensor moves to a reference position and is ready for measuring. In step S1004, the three-dimensional sensor measures the center of each chip or inspected area by scanning the tray back and forth in the X-axis direction, and the sampled signals are taken. In step S1006, the sampled signals of each chip or inspected area are processed and averaged to determine the focusing position of each chip or inspected area. The focusing position is then stored in a database. In step S1008, an image sensor moves to a reference point. In step S1010, the averaged focusing position of the next inspected chip or inspected area is retrieved from the database. In step S1012, the focus of the image sensor is adjusted to the images of chips by the focusing positions. In step S1014, the image sensor inspects back and forth in the Y-axis direction. In step S1016, the images are obtained. In step S1018, the images are analyzed and compared by an image analysis unit. In step S1020, the system determines whether the inspection process is completed. If the process is completed, the program is terminated. In step S1022, the image sensor moves to next chip or inspected area, and the system performs steps S1010-S1020 again.

The above-described embodiments of the present invention are intended to be illustrative only. Numerous alternative embodiments may be devised by person skilled in the art without departing from the scope of the following claims.

What is claimed is:

1. A system for inspecting chips in a tray, comprising:
   a three-dimensional sensor configured to provide a height signal of a surface of a chip in a tray;
   a focus computing unit configured to determine a focusing position of the surface of the chip by the height signal;
   an image sensor configured to inspect the surface of the chip; and
   a focusing device configured to position the image sensor to perform a focusing operation based on the focusing position, wherein the image sensor is attached to the focusing device.

2. The system of claim 1, wherein the focusing device is a Z stage.

3. The system of claim 1, further comprising:
   an XY stage; and
   a Z stage disposed on the XY stage and configured to provide Z-axis direction movement;
   wherein the three-dimensional sensor is disposed on the Z stage.

4. The system of claim 1, further comprising:
   an XY stage, wherein the focusing device is disposed on the XY stage and the image sensor can scan the surface of the chip by the XY stage.

5. The system of claim 1, wherein the three-dimensional sensor is a chromatic sensor.

6. The system of claim 1, further comprising a transfer mechanism, wherein the transfer mechanism comprises:
   a tray track configured to keep the tray moving in a predetermined direction;
   a push bar mechanism comprising:
      a linear driving apparatus; and
      a push bar stretched over the tray track and attached to the linear driving apparatus, wherein a portion of the push bar above the tray track includes a contact part, and when the push bar moves, the contact part pushes the tray to move along the tray track;
   a positioning apparatus comprising a plurality of extruded parts, wherein when the extruded parts protrude into the tray track, the extruded parts adjust the position and orientation of the tray placed in between by exerting lateral forces; and
   a pinch roller mechanism comprising:
      an elastic member; and
      a pinch roller attached to the elastic member, wherein the elastic member provides a pressing force for pressing the tray via the pinch roller.

7. The system of claim 6, wherein the contact part comprises a plurality of vertical pins.

8. The system of claim 6, wherein the elastic member is a spring arm.

9. The system of claim 6, wherein the positioning apparatus further comprises an up/down movement mechanism.

10. The system of claim 9, wherein the up/down movement mechanism is a linear motor, a hydraulic cylinder or an electrical actuator.

11. The system of claim 1, wherein a surface deviation of the tray track is less than 5 micrometers.

12. The system of claim 1, further comprising an image analysis unit configured to analyze an image obtained by the image sensor and to record a defective chip location.

13. The system of claim 1, wherein the image sensor is a charge coupled device or a complementary metal oxide semiconductor sensor.

14. The system of claim 1, further comprising a chip pickup apparatus configured to remove a defective chip from the tray.

15. The system of claim 14, wherein the chip pickup apparatus further comprises a vacuum nozzle end effector.

16. The system of claim 1, further comprising a tray handling apparatus for loading and unloading, wherein the tray handling apparatus for loading and unloading comprises:
   an elevator apparatus configured to provide a tray stack up and down movement; and
   a loading arm configured to move the tray into or out of the tray stack.

17. The system of claim 16, wherein the elevator apparatus comprises a lead screw/servomotor combination.

18. The system of claim 1, further comprising an alignment arm configured to align the tray into the tray track.

19. The system of claim 1, further comprising a database configured to store the height signal, the focusing position and an image obtained by image sensor.

20. The system of claim 1, wherein the three-dimensional sensor is disposed on the focusing device.

21. A method for inspecting chips in a tray, comprising the steps of:
   scanning a plurality of chips in a tray and obtaining a height signal of each chip by a three-dimensional sensor;
   processing the height signal of each chip to determine focusing position thereof by a focus computing unit;
   adjusting a focus of an image sensor by a focusing device based on the focusing position of each chip; and
   inspecting the surface of each chip by the image sensor.

22. The method of claim 21, further comprising the steps of:
   obtaining a surface image of each chip by the image sensor;
   analyzing the surface image of each chip; and
   removing a chip disqualified by a negative imaging analysis result.

23. The method of claim 21, further comprising the steps of:
   moving the tray to a place above which a positioning apparatus is located; and
   protruding extended parts of the positioning apparatus for adjusting the position and orientation of the tray.

24. The method of claim 21, further comprising the steps of:
   lowering the tray by an elevator apparatus; and
   moving the tray out of a tray handling apparatus for loading by a loading arm.

25. The method of claim 21, further comprising the steps of:
   moving the tray into a tray handling apparatus for unloading from a tray stack by a loading arm; and
   moving the tray up against the tray stack by an elevator apparatus.

26. The method of claim 21, further comprising the step of:
   aligning the tray to a tray track by pushing the tray against an elongated metal plate of the tray track.

* * * * *